United States Patent [19]

Moore et al.

[11] Patent Number: 4,545,679
[45] Date of Patent: Oct. 8, 1985

[54] FREQUENCY SHIFT MEASUREMENT IN SHOCK-COMPRESSED MATERIALS

[75] Inventors: David S. Moore; Stephen C. Schmidt, both of Los Alamos, N. Mex.

[73] Assignee: The United States of America as represented by the United States Department of Energy, Washington, D.C.

[21] Appl. No.: 581,934

[22] Filed: Feb. 21, 1984

[51] Int. Cl.[4] ............................................. G01N 21/65
[52] U.S. Cl. ................................................... 356/301
[58] Field of Search ....................................... 356/301

[56] References Cited

U.S. PATENT DOCUMENTS 4,398,801  8/1983  McWilliams et al. .............. 350/275

OTHER PUBLICATIONS

Schmidt et al., Los Alamos Unclassified Report 83-901, presented at the Workshop on Shock-Compression Chemistry in Materials Synthesis and Processing, Battelle Conference Center, Seattle, Wa., Mar. 28-29, 1983.
Schmidt et al., Los Alamos Unclassified Report 83-1584, presented at the Conference on Shock-Waves in Condensed Matter, Santa Fe, NM, Jul. 18-21, 1983.
Moore et al., Los Alamos Unclassified Report 83-1854, presented at the *IX AIRAPT Conference*, Albany, NY, Jul. 25-29, 1983.
Schmidt et al., Los Alamos Unclassified Report 83-2847, presented at the CEA/Los Alamos High Explosives and Detonation Physics Conference, Paris, France, Oct. 3-6, 1983.
Maier et al., "Backward Stimulated Raman Scattering", *Physical Review*, vol. 177, No. 2, Jan. 10, 1969, pp. 580-599.
Keeler et al., "Stimulated Brillouin Scattering in Shock-Compressed Fluids", *Physical Review Letters*, vol. 17, No. 16, Oct. 17, 1966, pp. 852-854.
Bloom et al., "Stimulated Brillouin Scattering in Shock-Compressed Fluids", *Journal of Applied Physics*, vol. 45, No. 3, Mar. 1974, pp. 1200-1207.
Moore et al., Los Alamos Unclassified Report 83-1024, Apr. 7, 1983, also published in the Proceedings of the Los Alamos Conference on Optics '83.
Schmidt et al., "Backward Stimulated Raman Scattering in Shock-Compressed Benzene", *Physical Review Letters*, vol. 50, No. 9, Feb. 28, 1983, pp. 661-664.
Moore et al., *Physical Review Letters*, vol. 50, No. 22, May 30, 1983, pp. 1819-1822.
Schmidt et al., Los Alamos Unclassified Report 83-351, presented at the Ninth International Colloquium on Dynamics of Explosions and Reactive Systems, Poitiers, France, Jul. 4-8, 1983.

*Primary Examiner*—F. L. Evans
*Attorney, Agent, or Firm*—William A. Eklund; Paul D. Gaetjens; Judson R. Hightower

[57] ABSTRACT

A method for determining molecular vibrational frequencies in shock-compressed transparent materials. A single laser beam pulse is directed into a sample material while the material is shock-compressed from a direction opposite that of the incident laser beam. A Stokes beam produced by stimulated Raman scattering is emitted back along the path of the incident laser beam, that is, in the opposite direction to that of the incident laser beam. The Stokes beam is separated from the incident beam and its frequency measured. The difference in frequency between the Stokes beam and the incident beam is representative of the characteristic frequency of the Raman active mode of the sample. Both the incident beam and the Stokes beam pass perpendicularly through the shock front advancing through the sample, thereby minimizing adverse effects of refraction.

5 Claims, 2 Drawing Figures

FREQUENCY SHIFT MEASUREMENT IN SHOCK-COMPRESSED MATERIALS

This invention is the result of a contract with the U.S. Department of Energy (Contract No. W-7405-ENG-36).

BACKGROUND OF THE INVENTION

The invention disclosed herein is generally related to methods and apparatus for the spectroscopic analysis of shock-compressed materials. More specifically, this invention is related to the analysis of shock-compressed transparent liquids and solids by the use of a technique known as backward-stimulated Raman scattering.

A continuing long-term mission of the Los Alamos National Laboratory is the study of the chemical and physical characteristics of materials at high temperatures and pressures, particularly temperatures and pressures such as those which exist in high explosive detonations. Such characteristics are useful for determining equations of state for the materials and for predicting the behavior of the materials, particularly high explosives, in various configurations and environments. Under such conditions intramolecular and intermolecular forces change considerably and nonequilibrium conditions may be expected. Chemical behavior may be dramatically different from that expected from either extrapolations from ambient conditions or thermodynamic equilibrium calculations. Accordingly, it has been sought to develop fast nonlinear optical techniques to study high-pressure processes which are governed by transient and possibly nonequilibrium phenomena.

For many purposes, it is sufficient and useful to determine the physical and chemical characteristics of materials which are shock-compressed to high pressures by mechanical means rather than by the use of explosives, thus enabling simpler and safer experiments to be conducted under controlled conditions which to some extent simulate the conditions in a high explosive detonation. The present invention is directed to a novel spectroscopic technique which employs such a mechanical shock means, and which is particularly useful for determining vibrational frequencies of shock-compressed materials.

Several optical diagnostic techniques have been previously used to study shock-compressed materials. For example, both emission and absorption spectroscopy have been used for this purpose. However, these techniques suffer from the disadvantage of low signal strengths against high backgrounds. Also, many molecular vibrational transitions occur in the infrared region of the spectrum, where detection systems are not fast enough for the very short time periods available during shock-compression experiments. Optical fluorescence and phosphorescence techniques have also been proposed for the purpose of studying shock-compressed systems, but as yet have only been applied to statically compressed systems.

Several techniques which have been either proposed or actually applied to shock-compressed systems are based on the phenomenon of Raman scattering. Raman scattering is the inelastic scattering of light from molecules. In this regard, light impinging on a molecule is ordinarily scattered elastically, without undergoing any change in frequency, by a scattering process known as Rayleigh scattering. However, a small fraction of the light may undergo inelastic, or Raman scattering at a different frequency. More specifically, in Raman scattering a portion of the energy of the incident photon is typically absorbed by the molecule, resulting in the scattered photon having a lower energy and longer wavelength than that of the impinging photon. In some cases the incident photon absorbs energy from the molecule, resulting in the scattered photon having a higher energy and shorter wavelength than the incident photon.

In both the Rayleigh and the Raman scattering processes, the molecule is momentarily excited by the incident photon to an excited, or virtual, energy level. In Rayleigh scattering the molecule decays back to the initial energy level, whereas in Raman scattering the molecule decays to an excited vibrational level which is typically the $v=1$ vibrational state. The difference in energy between the incident photon and the emitted Raman photon is equal to the energy difference between the ground vibrational state and the $v=1$ vibrational state.

The scattering cross-section and hence the detection sensitivity for Raman scattering are considerably smaller than for dipole emission/absorption processes. The small scattering cross-section is particularly significant when the scattering medium has a high background emission level, such as might be the case in a hot shock-compressed material. This difficulty can be overcome to some extent by using a short-wavelength exciting frequency. However, care must be taken to avoid interfering fluorescence from photochemically produced species.

Raman scattering is ordinarily isotropic, i.e., the scattered radiation is emitted uniformly over $4\pi$ steradians. However, it has been observed that, when a laser beam is focused in a sample of material, and when the incident laser intensity exceeds a certain threshold level, coherent Raman scattering may occur along the axis of the incident beam. The intensities of these forward and backward directed beams is of considerably greater intensity than that of ordinary Raman scattering as a consequence of laser-like amplification in either direction along the path of the laser beam. Typical threshold intensities of the incident laser beam for stimulated Raman scattering are 10–100 GW/cm$^2$. As a consequence of the large scattering intensities and the beam-like nature of the scattered signal, there is the possibility of increased detection sensitivity and shorter temporal resolution limits.

A technique that is related to yet different from the present invention was developed by the applicants of the present invention and is disclosed and claimed in the applicants' U.S. patent application Ser. No. 562,150, filed Dec. 16, 1983.

The phenomenon of backward-stimulated Raman scattering is put to use in the method of the invention, which is described below.

SUMMARY OF THE INVENTION

It is an object and purpose of the present invention to provide a method for determining molecular vibrational frequencies in materials at very high pressures and temperatures.

It is also an object and purpose of the present invention to provide a method for determining molecular vibrational frequencies in shock-compressed liquids.

It is also an object and purpose of the present invention to provide a method for determining vibrational frequencies of molecular species as a function of pressure, from ambient atmospheric pressure up to pressures which are comparable to those which exist in high explosive detonations.

Additional objects, advantages and novel features of the invention will be set forth in part in the description that follows, and part will become apparent to those skilled in the art upon examination of the following detailed description or may be learned by practice of the method of the invention. The objects and advantages of the invention may be realized and attained by means of the instrumentalities and methods particularly pointed out in the appended claims.

To achieve the foregoing and other objects, and in accordance with the purposes of the present invention as embodied and broadly described herein, the present invention provides a method of determining molecular vibrational frequencies of shock-compressed materials. The method makes use of the phenomenon known as backward-stimulated Raman scattering (BSRS). In accordance with the method, a short duration incident laser beam is directed into a shock-compressed transparent sample of material, which may be either in the liquid or solid state. The intensity of the laser beam is sufficiently great to induce stimulated Raman scattering in the sample, resulting in an oppositely directed Stokes beam being emitted along the axis of the incident laser beam. Shock-compression is achieved in such a way as to create a shock wave which travels through the sample in a direction opposite to that of the incident laser beam. The duration of the incident laser pulse is much shorter than the time the sample remains in the shock-compressed state. The backward-stimulated Raman beam is separated from the incident beam and its frequency is measured.

In the preferred embodiment, the sample is destructively shock-compressed by means of a high velocity projectile fired from an air gun. The sample is shaped so that its dimensions in directions transverse to the direction of travel of the projectile and the path of the incident laser beam are large compared with the dimension of the sample in the direction along the path. The dimensions of the projectile are also preferably large in the direction transverse to the direction of travel of the projectile and the axis of the incident laser. This results in a substantially planar shock wave being created in the sample, and further results in the shock-compressed sample being substantially free of rarefaction waves, which would distort and refract both the incident laser beam and the Stokes beam.

A primary advantage of the present invention over other known spectroscopic methods for analyzing shock-compressed materials is that both the incident beam and the emitted Stokes beam pass perpendicularly through the plane of the advancing shock wave. Consequently, diffraction and accompanying distortion of the two beams is avoided. Also, the intensity of the Stokes beam is greater than ordinary, or non-stimulated Raman scattering, thus enabling greater detection sensitivity.

By using a projectile and sample which are wide in comparison with the depth of the sample, the shock-compressed region behind the shock wave can be analyzed free of the distortion that would otherwise be caused by rarefaction waves.

These and other aspects of the present invention are further disclosed and described in the detailed description of the invention set forth below.

BRIEF DESCRIPTION OF THE DRAWINGS

The accompaying drawings, which are incorporated in and form a part of this specification, illustrate the apparatus used to practice the preferred embodiment of the invention and, together with the following detailed description, serve to explain the principles of the invention. In the drawings.

DETAILED DESCRIPTION OF THE INVENTION

Figure 1:
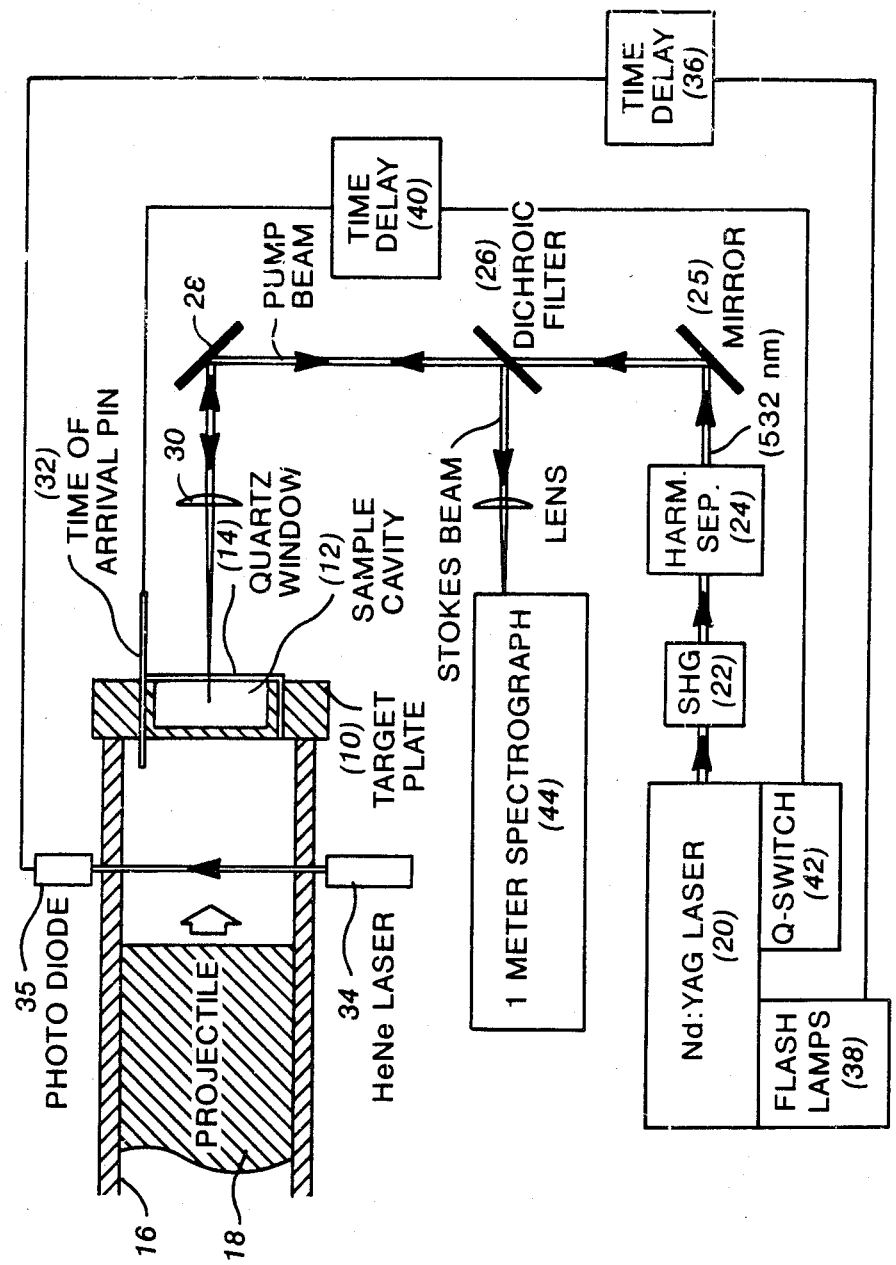
FIG. 1 is a schematic diagram of the apparatus used to practice the invention.

FIG. 1 illustrates an apparatus for the practice of the invention. The apparatus includes a target plate 10 which consists of a one-half inch thick aluminum disk having an 8-mm deep, 38-mm diameter central cylindrical cavity 12 opening onto one side. A liquid sample is contained in the cavity 12 by means of a 1-mm-thick quartz window 14. The target plate is mounted on the muzzle of a 3.3 meter-long, 51 mm-diameter gas gun 16. In operation, the gas gun 16 fires an approximately 300 gm aluminum projectile 18 at velocities of up to approximately 1 km/sec. Prior to firing the target plate 10 is sealed to the muzzle of the gun and the bore of the barrel is evacuated. The projectile 18, target plate 10 and disposable optical components located in front of the target plate are all destroyed by the impact of the projectile with each firing of the gun.

The impact of the projectile on the back of the target plate creates a substantially planar shock wave which travels through the liquid sample and out the quartz window at a speed several times the speed of the projectile and the disintegrating target plate. There is thus created momentarily a shock-compressed region in the liquid behind the moving shock wave. The shock-compressed region attains pressures on the order of 10 to 15 kilobars. During the few microseconds during which the shock-compressed region exists, backward-stimulated Raman scattering is induced in the shock-compressed region of the sample by means of a single-pulse laser beam which is directed into the sample through the quartz window, as described further below.

The incident laser beam, which is hereinafter referred to as the pump beam, is generated with a medium energy, neodymium-doped, yttrium aluminum garnet (Nd:YAG) pulsed laser 20. The beam from the laser 20 is frequency doubled with a second harmonic generator (SHG) 22. The frequency doubled beam is isolated with a harmonic separator 24. The resulting pump beam has a frequency of 532 nanometers, a pulse duration of ~6 ns (nanoseconds), and an energy of from 1-5 millijoules. The pump beam is reflected by a mirror 25 through a dichroic filter 26 to a second mirror 28, which is disposable and which directs the beam through a disposable lens 30 into the sample cavity 12. The lens 30 has a focal length of 6 inches and is positioned to focus the beam in the sample several millimeters behind the quartz window.

Timing of the pump beam pulse to coincide with the few microseconds during which the sample is shock-compressed is obtained by means of an electrical time-of-arrival pin 32 located in the sample plate, and by means of a helium-neon laser trigger 34 and associated photodiode 35 located approximately 25 cm up the barrel bore from target plate.

In operation, the passage of the projectile past the helium-neon laser trigger creates a signal which, after being delayed by a delay unit 36, activates flash lamps 38 associated with the Nd:YAG laser. The flash lamps are activated approximately 300 microseconds before the impact of the projectile against the target plate. The time-of-arrival pin 32, upon being subsequently struck by the projectile, creates a second timing signal which, after being delayed by a second delay unit 40, is applied to a Q-switch 42 associated with the Nd:YAG laser. The Q-switch 42 operates to release the 6-nanosecond pulse from the Nd:YAG laser. With the timing system just described, the laser pulse can be timed so as to be focused in the sample several millimeters behind the advancing shock wave, at a time when the shock wave is approximately 1 millimeter from the window.

The high intensity of the incident pump beam at the focal point, combined with a large cross-section Raman active mode in the sample, produces a coherent, stimulated Stokes beam in the direction opposite that of the incident beam. The frequency of the Stokes beam differs from the frequency of the pump beam by the characteristic frequency of the Raman active mode. The Stokes beam is directed back along the path of the pump beam to the dichroic filter 26, where it is separated from the pump beam and directed into a 1-meter-focal-length Czerny-Turner monochromator 44 and recorded on photographic film. The monochromator is equipped with a 1200-grooves/mm diffraction grating, which is used in first order.

It will be noted that a primary advantage of the present invention is that both the incident pump beam and the emitted Stokes beam pass perpendicularly through the shock front as well as the containment window. Consequently there is avoided any significant distortion or refraction caused by refractive index gradients in the shock front or the refractive index discontinuity at the window/sample interface.

Figure 2:
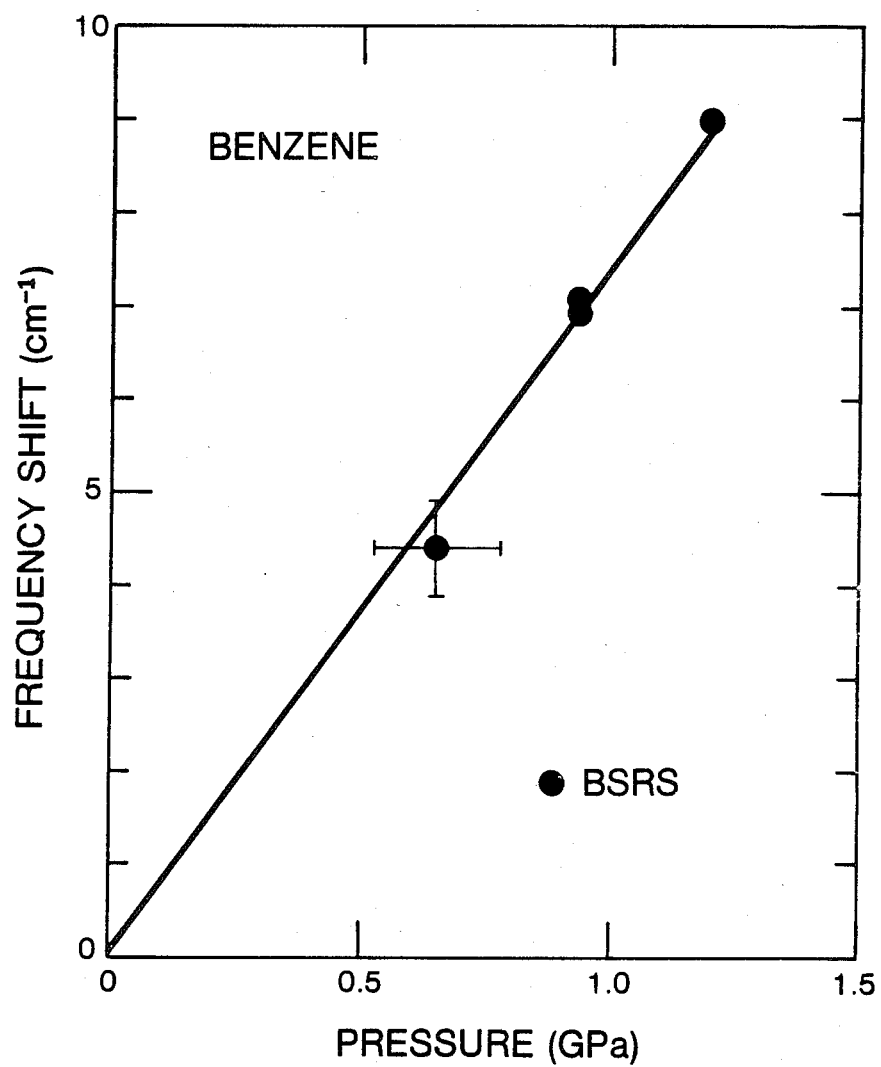
FIG. 2 presents the data obtained under unshocked and various shocked conditions from a benzene sample.

The present invention has been used to determine the variation of the symmetric ring-stretching frequency of benzene with pressure, up to pressures of approximately 15 kilobars, or 1.5 GPa. In liquid benzene, the symmetric ring-stretching mode, which has a characteristic frequency of approximately 992 cm$^{-1}$, has the lowest threshold for stimulated Raman scattering induced by 532-nm light, and consequently is the transition observed in the experiments. FIG. 2 presents data showing the variation of the characteristic ring-stretching frequency with pressure. The crossed lines on one data point indicate the range of uncertainties in the measurements.

The measurement of vibrational frequency shifts at extremely high pressures offers the opportunity of directly determining a single-mode Grüneisen parameter $\gamma_i$. This parameter is defined as $\gamma_i = -\partial \ln \nu_i / \partial \ln V$, where $\nu_i$ is the frequency of a vibrational mode and V is the specific volume of the material. The Grüneisen parameter is thus a measure of the variation of a molecular vibrational frequency with the specific volume of the material. The parameter is useful in equation-of-state calculations. As a result of the experiments conducted with benzene, it has been determined that the Grüneisen parameter for the ring-stretching mode of benzene increases by a factor of approximately 4 for a volume compression of 23%, which is the volume compression attained at the upper pressure limits of the experiments.

The foregoing description of a preferred embodiment of the invention has been presented for purposes of illustration and description. It is not intended to be exhaustive or to limit the invention to the precise form disclosed, and various modifications and substitutions may be made without departing from the essential invention. The embodiment described above is presented to best explain the principles of the invention and its practical application to as to enable those skilled in the art to utilize the invention. It is intended that the scope of the invention be defined by the claims set forth below.

What is claimed is:

1. A method of determining molecular vibrational frequencies in shock-compressed materials, comprising the steps of:
   applying a shock to a material sample so as to form a shock wave which travels through the sample;
   directing a pulsed laser beam into the shocked sample in a direction opposite to that of the direction of travel of the shock wave; and
   measuring, while the sample is shock-compressed, the frequency of the backward-stimulated Stokes beam emitted from the sample in the direction opposite to the direction of the laser beam.

2. The method defined in claim 1 wherein the backward-stimulated Stokes beam is separated from the laser beam by means of a dichroic filter.

3. The method defined in claim 1 wherein said shock is applied to the sample by means of a projectile, and wherein the dimensions of the sample and the projectile in directions transverse to the direction of said laser beam are large in comparison with the dimension of said sample in the direction of said laser beam, whereby said laser beam and said Stokes beam are not distorted by rarefaction waves in the sample.

4. The method defined in claim 3, wherein said shock wave formed in said sample is substantially planar, and wherein said laser beam and said Stokes beam are passed through a surface of said sample which is substantially parallel to said shock wave and normal to the direction of propagation of said shock wave.

5. The method of claim 1 wherein said pulsed laser beam has a duration which is small compared with the propagation time of said shock wave through said sample, and wherein said laser beam is timed and focused so as to be directed and focused into said sample at a location behind the advancing shock wave, at a time before the shock wave exits the sample.

* * * * *